US006855820B2

(12) United States Patent
Broom et al.

(10) Patent No.: US 6,855,820 B2
(45) Date of Patent: Feb. 15, 2005

(54) PHARMACEUTICALLY ACTIVE MORPHOLINOL

(75) Inventors: Toby Broom, Stevenage (GB); Monica Delpogetto, Verona (IT); Richard Atkins, Kent (GB); Alan Negus, Kent (GB); Paul William Oxley, Kent (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/147,588

(22) Filed: May 17, 2002

(65) Prior Publication Data

US 2003/0027827 A1 Feb. 6, 2003

(51) Int. Cl.[7] .................... C07D 295/22; A61K 31/535
(52) U.S. Cl. ........................ 544/173; 544/170; 514/58; 514/238.8
(58) Field of Search ............................. 544/173, 170; 514/58, 238.8

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,622,675 A | 11/1971 | Koppe et al. |
| 3,630,200 A | 12/1971 | Higuchi |
| 3,819,706 A | 6/1974 | Mehta |
| 3,845,770 A | 11/1974 | Theeuwes et al. |
| 3,885,046 A | 5/1975 | Mehta |
| 3,916,899 A | 11/1975 | Theeuwes et al. |
| 3,960,927 A | 6/1976 | Metcalf et al. |
| 4,008,719 A | 2/1977 | Theeuwes et al. |
| 4,347,176 A | 8/1982 | Mehta |
| 4,347,177 A | 8/1982 | Phillips |
| 4,347,178 A | 8/1982 | Findlay et al. |
| 4,347,257 A | 8/1982 | Stern |
| 4,347,382 A | 8/1982 | Scharver |
| 4,355,179 A | 10/1982 | Findlay et al. |
| 4,356,165 A | 10/1982 | Findlay et al. |
| 4,393,078 A | 7/1983 | Peck |
| 4,425,363 A | 1/1984 | Stern |
| 4,435,449 A | 3/1984 | Stern |
| 4,438,138 A | 3/1984 | Stern |
| 4,507,323 A | 3/1985 | Stern |
| 4,571,395 A | 2/1986 | Peck |
| 4,656,026 A | 4/1987 | Coffman et al. |
| 4,687,660 A | 8/1987 | Baker et al. |
| 4,769,027 A | 9/1988 | Baker et al. |
| 4,798,826 A | 1/1989 | Peck |
| 4,835,147 A | 5/1989 | Roberts |
| 4,868,344 A | 9/1989 | Brown |
| 4,895,845 A | 1/1990 | Seed |
| 4,935,429 A | 6/1990 | Dackis et al. |
| 4,935,439 A | 6/1990 | Kashman et al. |
| RE33,994 E | 7/1992 | Baker et al. |
| 5,217,987 A | 6/1993 | Berger |
| 5,358,970 A | 10/1994 | Ruff et al. |
| 5,399,765 A * | 3/1995 | Gao et al. .................. 564/365 |
| 5,427,798 A | 6/1995 | Ludwig et al. |
| 5,447,948 A | 9/1995 | Seibyl et al. |
| 5,512,593 A | 4/1996 | Dante |
| 5,541,231 A | 7/1996 | Ruff et al. |
| 5,648,347 A | 7/1997 | Mehta et al. |
| 5,731,000 A | 3/1998 | Ruff et al. |
| 5,753,712 A | 5/1998 | Pinsker |
| 5,763,493 A | 6/1998 | Ruff et al. |
| 6,274,579 B1 | 8/2001 | Morgan et al. ........... 514/238.8 |
| 6,337,328 B1 | 1/2002 | Fang et al. ............... 514/231.2 |
| 6,342,496 B1 * | 1/2002 | Jerussi et al. ............ 514/231.2 |
| 6,391,875 B2 | 5/2002 | Morgan et al. ........... 514/238.8 |
| 2002/0052340 A1 | 5/2002 | Jerussi et al. .................. 514/58 |
| 2002/0052341 A1 * | 5/2002 | Fang et al. .................... 514/58 |

FOREIGN PATENT DOCUMENTS

| | | |
|---|---|---|
| CA | 977777 | 11/1975 |
| CA | 977778 | 11/1975 |
| EP | 0 118 036 | 9/1984 |
| EP | 0 170 430 A1 | 2/1986 |
| EP | 0 171 227 | 2/1986 |
| EP | 0 467 488 | 1/1992 |
| JP | 63-91352 | 4/1988 |
| WO | 91/11184 | 8/1991 |
| WO | 92/18489 | 10/1992 |
| WO | 92/19226 | 11/1992 |
| WO | 93/21917 | 11/1993 |
| WO | 94/04138 | 3/1994 |
| WO | 94/20100 | 9/1994 |
| WO | 95/03791 | 2/1995 |
| WO | 95/22324 | 8/1995 |
| WO | 96/39133 | 12/1996 |
| WO | 97/29735 | 8/1997 |
| WO | 98/50044 | 11/1998 |
| WO | 99/37305 | 7/1999 |
| WO | 01/62257 | 8/2001 |

OTHER PUBLICATIONS

Golden et al., "Bupropion in Depression," Arch. Gen Psychiatry, vol. 45, Feb. 1988.

Laizure, et al., "Pharmacokinetics of bupropion and its major basic metabolites in normal subjects after a single dose," Clin. Pharm. Ther., 1985 (38), pp. 586–589.

Suckow, et al., "Enantiomeric Determination of the Phenylmorpholinol Metabolite of Bupropion in Human Plasma Using Coupled Achiral–Chiral Liquid Chromatography," Biomedical Chromatography, 1997, vol. 11, pp. 174–179.

Welch, et al., "Phmaracological significance of the species difference in bupropion metabolism," Xenobiotica, 1987, vol. 17, No. 3, pp. 287–298.

(List continued on next page.)

Primary Examiner—Dwayne Jones
(74) Attorney, Agent, or Firm—Bonnie L. Deppenbrock

(57) ABSTRACT

Disclosed is the compound (+)-(2S,3S)-2-(3-chlorophenyl)-3,5,5-trimethyl-2-morpholinol and pharmaceutically acceptable salts and solvates thereof, methods for preparing them, pharmaceutical compositions comprising them, and processes for their preparation; also disclosed is a method of treating depression, attention deficit hyperactivity disorder (ADHD), obesity, migraine, sexual dysfunction, Parkinson's disease, Alzheimer's disease, or addiction to cocaine or nicotine-containing (especially tobacco) products using such compound, salts, solvates or compositions.

18 Claims, 3 Drawing Sheets

OTHER PUBLICATIONS

Suckow, et al., "Pharmacokinetics of Bupropion and Metabolites in Plasma and Brain of Rats, Mice, and Guinea Pigs," *The American Society for Pharmacology and Experimental Therapeutics,* 1986, vol. 14, No. 6, pp. 692–697.

Posner, J., et al., "The Deposition of Bupropion and Its Metabolites in Healthy Male Volunteers After_and Multiple Doses," *Eur. J. Clin. Pharmacol.,* 1985, vol. 29, pp. 97–103.

Ascher, J.A., et al., "Bupropion: A Review of its Mechanism of Antidepressant Activity," *J. Cling. Psych.,* 1995, vol. 56, pp. 395–401.

Boswell, G. Evan, et al., "Synthesis and Anti–tetrabenazine Activity of C–3–e Analogues of Dimethyl–2–phenylmorpholines," *J. Heterocyclic Chem.,* vol. 33, pp. 33–39, 1993.

Boswell, G. Evan, et al., "Synthesis, Stereochemistry and Anti–tetrabenazine Activity of Bicyclo Analogues_2–phenylmorpholines," *J. Heterocyclic Chem.,* vol. 34, pp. 1813–1820, 1992.

Martin et al., "Antidepressant Profile of Bupropion and three Metabolites in Mice," *Pharmacopsychiatry,* 1990, vol. 23, pp. 187–194.

Eisman, et al., "The Isolation and Identification of Some Basic Urinary Metabolites of Bupropion–HCL in Man," *Pharmacologist,* 1979, vol. 21, p. 191.

Cooper et al., "Behavioral and Biochemical Effects of the Antidepressant, Bupropion (Wellbutrin): Evidence for Selective Blockade of Dopamine Uptake in Vivo," *The Journal of Pharmacology and Experimental Therapeutics,* 1980, vol. 215, No. 1.

Ferris et al., "Some Neurochemical Properties of a New Antidepressant, Bupropion Hydrochloride (Wellbutrin)," *Drug Development Research,* 1981, vol. 1, pp. 21–35.

Maxwell, et al., "Bupropion," *Pharmacol & Biochem Properties Drug Substances (M E Goldberg, Ed),* Am Pharm Assoc. Pub., Washington, 1981, vol. 3, pp. 1–55.

Findlay, et al., "Pharmacokinetics of Bupropion, a Novel Antidepressant Agent, Following Oral Administration to Healthy Subjects," *European Journal of Clinical Pharmacology,* 1981, vol. 21, pp. 127–135.

Butz, et al., "Radioimmunoassay and Pharmacokinetic Profile of Bupropion in the Dog," *The Journal of Pharmacology and Experimental Therapeutics,* 1981, vol. 217, No. 3.

Ferris et al., "Bupropion: A New Antidepressant Drug, The Mechanism of Action of Which is Not associated with Down–Regulation of Postsynaptic β–Adrenergic, Serotonergic (5–HT$_2$), β2–Adrenergic, Imipramine and Dopaminergic Receptors in Brain," *Neuropharmacology,* 1983, vol. 22, No. 11, pp. 1257–1267.

Mehta, "The Chemistry of Bupropion," *J. Clinical Psychiatry,* May 1983, 44:5 (Sec. 2).

Schroeder, David, "Metabolism and Kinetics of Bupropion," *J. Clinical Psychiatry,* May 1983, 44:5 (Sec. 2).

Lai, et al., "Clinical Pharmacokinetics of Bupropion: A Reivew," *J. Clinical Psychiatry,* May 1983, 44:5 (Sec. 2).

Cooper et al., "Determination of Bupropion nd Its Major Basic Metabolites in Plasma by Liquid Chromatography with Dual–Wavelength Ultraviolet Detection," *Journal of Pharmaceutical Sciences,* Aug. 1984, vol. 73, No. 8.

Laizure et al., "Stability of Bupropion and its Major Metabolites in Human Plasma," *Therapeuytic Drug Monitoring,* 1985, vol. 7, pp. 447–450.

Cooper et al., "Bupropion: Possible Rose of Major Metabolites in Mode of Action," *Clin. Pharmacol. Ther.,* Feb. 1985, vol. 37, No. 2.

DeVane, et al., "The Effect of Experimentally–Induced Renal Failure on Accumulation of Bupropion and its major basic metabolites in plasma and brain of guinea pigs," *Psychopharmacology,* 1986, vol. 89, pp. 404–408.

Perumal, et al., "Effect of Plasma from Patients Contianing Bupropion and its Metabolites on the Uptake of Norepinephrine," *Neuropharmacology,* 1986, vol. 25, No. 22, pp. 199–202.

Thomas Smith et al., "Brain regional [$^3$H]flunitrazepam binding in rats chronically treated with bupropion or B.W.306U," *Brain Research,* 1986, 367, pp. 385–389.

Ferris et al., "Mechanism of Antidepressant Activity of Bupropion," *J Clin Psychiatry Monograph,* 1993, vol. 11, pp. 2–14.

Musso, et al., Synthesis and Evaluation of the Antidepressant Activity of the Enantiomers of Bupropion, *Chirality,* 1993, vol. 5, pp. 495–500.

Hsyu, et al., "Pharmacokinetics of Bupropion and its Metabolites in Cigarette Smokers versus Nonsmokers," *J. Clin. Pharmacol.,* 1997, vol. 37, pp. 737–743.

Modell, et al., "Comparative sexual side effects of bupropion, fluoxetine, paroxetine, and sertraline," *Clinical Pharmacology & Therapeutics,* 1996, vol. 61, No. 4.

Cooper, et al., "Evidence that the Acute Behavioral and Electrophysiological Effects of Bupropion (Wellbutrin) are Mediated by a Noradrenergic Mechanism," *Neuropsychopharmacology,* 1994, vol. 11, No. 2, 99133–141.

Bannon et al., 1998, "Broad–spectrum, non–opoid analgesic activity by selective modulation of neuronal nicotinic acetylchroline receptors," *Science,* vol. 279, pp. 77–81.

Bischoff et al., 1984, "Affinity changes of rat striatal dopamine receptor in vivo after acute bupropion treatment," *Eur. J. Pharmaco.,* vol. 104, pp. 173–176.

Blondel–Hill et al., 1993, "Treatment of the chronic fatigue syndrome," *Drugs,* vol. 46, No. 4, pp. 639–651.

Borowski, T.B., et al., 1993, Amphetamine and antidepressant drug effects of GABA—and NMDA—related seizures, *Brain Res. Bull.,* vol. 30, pp. 607–610.

Calabrese, J.R. et al., 1991, "Treatment of depression," *Primary Care,* vol. 18, No. 2, pp. 421–433.

Castaldi, G. et al., 1987, "Tataric acid and efficient chiral auxillary: new asymmetric synthesis of 2–alkyl–2–arylacetic acids," *J. Org. Chem.,* vol. 52, p. 3018.

Castello, R.A., and Mattons, A.M., *J. Pharm. Sci.,* vol. 51, No. 2, pp. 106–108 (1962).

Charney, D.S. et al., 1983, "Monoamine receptor sensitivity and depression: clinical studies of antidepressant effects on serotonin and noradrenergic function," *Psychopharmac. Bull,* 19(3)p. 490.

Clay et al., 1988, "Clinical and neuropsychological effects of the novel antidepressant bupropion," *Psychopharma. Bull.,* 24(1), pp. 143–148.

Conners, K.C. et al., 1996, "Bupropion hydrochloride in attention deficit disorder with hyperactivity," *J. Am. Acad. Child Adolesc. Psychiatr.,* 34(10), pp. 1314–1321.

Cooke, C.E., 1997, Therapeutic advances in the treatment of cigarette addiction, *J. Pharmacy Practice,* 10(5) pp. 329–337.

Cooper, T.B. et al., Analytical psychopharmacology: NY State Psychiatric Institute, pp. 1–3, 1988.

Coutts, R.T. & Baker, G.B., 1989, "Implications of chirality and geometric isomerisms in some psychoactive drugs and their metabolites," *Chirality*, 1, pp. 99–120.

Crenshaw et al., 1987, "Pharmacological modification of psychosexual dysfunction," *J. Sex. Marital Ther.*, 13(4), pp. 239–252.

Cusack, B. et al., 1994, "Binding of antidepressants to human brain receptors: focus on newer generation compounds," *Psychopharmacol.*, 114, pp. 559–565.

Davidson et al., 1994, "Bupropion in chronic low back pain," *J. Clin. Psychiatry*, 55(8), p. 362.

Dilsaver, S.C. et al., 1992, "The efficacy of bupropion in winter depression: results of an open trial," *J. Clin. Psychiatry*, 53(7), pp. 252–255.

Eliel, E.L., 1962, *Stereochemistry of Carbon Compounds*, McGraw-Hill, NY.

Ferris, R.M. et al., 1983, "Studies of bupropion's mechanism of antidepressant activity," *J. Clin. Psychiatry*, 44(5), pp. 74–78.

Ferry, L.H. et al., 1992, "Enhancement of smoking cessation using the anti-depressant bupropion-hydrochloride," (abstract) Curculation 86:671.

Ferry, L.H. et al., 1994, "Efficacy of bupropion for smoking cessation in non-depressed smokers," *J. Addict, Dis.* 13:A9.

Fisher, R.S., 1989, "Animal models of epilepsies," *Brain Res. Reviews*, 14:245–278.

Foote et al., 1984, "Proconvulsant effect of morphine on seizures induced by pentlyenetetrazol in the rat," 105:179–184.

Garland et al., 1998, "Pharmacotherapy of adolescent attention deficit hyperactivity disorder: challenges, choices and caveats," *J. Psychopharmacology*, 12(4):385–395.

Goetz et al., 1984, "Bupropion in Parkinson's Disease," 34:1092–4.

Goodnick, P.J., 1994, "Pharmacokinetic optimisation of therapy with newer antidepressants," *Clin. Pharmacokinet.* 27(4):307–330.

Goodnick, P.J. & Sandoval, R., 1993, "Psychotropic treatment of depression: results of an open trial," *J. Clin. Psych.* 54(1):13–20.

Green, A.R. & Murray, T.K., 1989, "Asimple intravenous infusion method in rodents for determining potency of anticonvulsants acting through GABAergic mechanisms," *J. Pharm. Pharmacol.* 41:879–880.

Grimes et al., 1996, "Spontaneous orgasm with the combined use of bupropion and serttaline," *Soc. Biol. Psych.* 40:1184–1185.

*Handbook of Pharmaceutical Excipients*, 2$^{nd}$ ed., Wade and Willer eds, pp. 257–259 (1994).

Hsyu, P.H. et al., Nov. 10, 1997 Chemical Abstracts 127(19): Abstract No. 257089; Columbus, Ohio.

Janowsky, A., et al., *J. Neurochem.* 45:1272–1276 (1986).

Kelley, J.K. et al., 1996, "(2S,3S,5R)–2–(3,5–difluorophenyl)–3,5,–dimethyl–2–morpholinol: a novel antidepressant agent and selective inhibitor of norepiniphrine uptake," *J. Med. Chem.* 39:347–349.

Ketter, T.A. et al., 1995, "Carbamazepine but not valproate induces bupropion metabolism," *J. Clin. Psychopharmacol.* 15(5):327–333.

Lief, H.I., 1996, "Bupropion treatment of depression to assist smoke cessation," *Am. J. Psychiatry* 153(3):442.

Little, K.Y. et al., 1993, "[$^{125}$I]RTI–55 binding to cocaine-sensitive dopaminergic and serotonergic uptake sites in the human brain," *J. Neurochem.* 61:1996–2006.

McNamee et al., 1986, "Stimulation of substrate oxidation in rat hepatic mitochondria following pretreatment with apetite modifying drugs," *J. Pharm. Pharmacol.* 37:147.

Merskey, H., 1965, "The effect of chronic pain upon the response to noxious stimuli by psychiatric patients," *J. Psychosom. Res.*, 8:405–419.

Mitchell, G.F. et al., 1989, "Effect of bupropion on chocolate craving," *Am. J. Psychiatry*, 146(1):119–120.

Mitchell, G.F. et al., 1989, "Dr. Mitchell and associates reply," *Am. J. Psychiatry*, 146(8):1089.

Moisset, B. et al., *Brain Res.*, 92:157–164 (1975).

Moret, C. & Brile, M., 1988, "Sensitizing of the response of 5–HT autoreceptors to drugs modifying synaptic availability of 5–HT", 27(1):43–49.

Musso et al., 1997, "Synthesis and Evaluation of the Anticonvulsant Activity of a Series of 2–Amino–Phenyl–1–Propanols Derived from the Metabolites of the Antidepressant Bupropion," *Bioorganic & Medical Chemistry Letters*, vol. 7 No. 1, pp. 1–6, 1997.

*Neurology*, Official Journal of American Academy of Neurology, Aug. 1984, vol. 34, No. 8.

Nomikos, et al., 1992, "Effects of chronic bupropion in interstitial concentrations of dopamine in rat nucleus accumbens and striatum," *Neuropsychopharmacology* 7(1):7–14.

Nutt, D.J. et al., 1981, "Studies on the postietal rise in seizure threshold," *Eur. J. Phamacol.*, 71:287–295.

Nutt et al., 1980, "On the measurement in rats of the convulsant effect of drugs and the changes which follow electroconvulsive shock," *Neuropharmacology* 19:1017–1023.

Olsen et al., 1985, "Benzodiazepine/γ–aminobutyric acid receptor deficit in the midbrain of the seizure–susceptible gerbil," *PNAS USA* 82:6701–6705.

Pearlstein et al., 1997, "Comparison of fluoxetine, bupropion, and placebo in the treatment of premenstrual dysphoric disorder," *J. Clin. Psychopharmacol.* 17(4):261–266.

*Physicians Desk Reference®*, 1998, pp. 1120–11274.

Popli, A.P., et al., 1994, "Antidepressant–associated seizures," *J. Clin. Psych.* 55(6):267.

Popli, A., et al., 1995, "Bupropion and anticonvulsant drug interactions," *Annals of Clin. Psychiatr.* 7(2):99–101.

Potter, W.Z. & Janji, H.K., 1990, "Antidepressants, metabolites, and apparent drug resistance," *Clin. Neuropharmacol.*, 13(1):S45–S53. 82:6701–6705.

*Remingtons: The Practice of the Science and Pharmacy*, 19$^{th}$ ed., Gennaro, eds., p1625 (1995).

Rose, J.E., 1996, "Nicotine addiction and treatment," *Annu. Rev. Med.*, 47:493–507.

Rosenstein, D.L., et al., 1993, "Seizure associated with antidepressants: a review," *J. Clin. Psychiatry* 54(8): 289–299.

Rudorfer, M.V. et al., 1994, "Comparative tolerability profiles of the newer versus older antidepressants," *Drug Safety* 10(1):18–46.

Schroeder, D.H., 1979, "The isolation and identification of some basic urinary metabolites of bupropion—HCL in man," *The Pharmacologist* 21(3):191.

Scrip Bupropion Sustained Release (SR) for Smoking Cessation, Dec. 18, 1996.

Scrip Itraconazole for pulse dosing of onychomycosis, Dec. 18, 1996.

Scrip's New Product Review, No. 50 Bupropion, PJB Publications: United Kingdom, Aug., 1990.

Stathis, M. et al., 1995, "Rate of binding of various inhibitors at the dopamine transporter in vivo," *Psychopharmacol.,* 119:376–384.

Storrow, A.B., 1994, "Bupropion overdose and seizure," *Am. J. Emerg. Med.,* 12:183–184.

Sulser, F., 1983, "Molecular mehcanisms in antidepressant action," *Psychopharmacol. Bull.* 19(3):300.

Sweet, R.A., et al., 1995, "Pharmacokinetics of single–and multiple–dose bupropion in elderly patients with depression," *J. Clin. Pharmacol.,* 35:876–884.

Testa, B. and Trager, W.F., 1990, "Racemates Versus Enantiomers in Drug Development: Dogmatism or Pragmatism?" *Chirality* 2:129–133.

Vassout, A., et al, 1993, "Regulation of dopamine receptors by bupropion comparison with antidepressants and CNS stimulants," *J. Rceptor Res.,* 13(1–4):341–354.

Ward, N.G., 1990, *The Management of Pain,* Second Edition, vol. 1, chapter 18 (eds.) Bonica, J.J. pp. 310–319.

Ward, R., et al., 1971, Asymmetric audiogenic seizures in mice: a possible analogue of focal epilepsy, *Brain Res.,* 31:207–210.

Wilen, S.H., 1972, *Tablets of Resolving Agents in Optical Resolutions,* Univ. of Notre Dame Press, Notre Dame, IN.

Wright et al., 1985, "Bupropion in the long–term treatment of cyclic mood disorders: mood stabilizing effects," *J. Clin. Psych.* 46(1):22–25.

Zarrindast et al., 1988, "Anoretic and behavioral effects of bupropion," *Gen. Pharmacology,* 19(2):201–204.

\* cited by examiner

PHARMACEUTICALLY ACTIVE MORPHOLINOL

BACKGROUND OF THE INVENTION

Bupropion hydrochloride, (±)-1-(3-chlorophenyl)-2-[(1,1-dimethylethyl)-amino]-1-propanone hydrochloride, is the active ingredient of Wellbutrin® which is marketed in the United States for the treatment of depression. It is also the active ingredient of Zyban® which is marketed in the United States as an aid to smoking cessation. Bupropion is a relatively weak inhibitor of the neuronal uptake of noradrenaline (NA), serotonin and dopamine (DA), and does not inhibit monoamine oxidase. While the mechanism of action of bupropion, as with other antidepressants, is unknown, it is presumed that this action is mediated by noradrenergic and/or dopaminergic mechanisms. Available evidence suggests that Wellbutrin® is a selective inhibitor of noradrenaline (NA) at doses that are predictive of antidepressant activity in animal models. See Ascher, J. A., et al., Bupropion: A Review of its Mechanism of Antidepressant Activity. *Journal of Clinical Psychiatry*, 56: p. 395–401,1995.

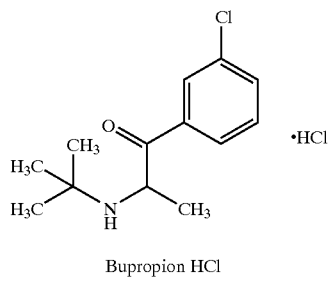

Bupropion HCl

Bupropion is extensively metabolized in man as well as laboratory animals. Urinary and plasma metabolites include biotransformation products formed via hydroxylation of the tert-butyl group and/or reduction of the carbonyl group of bupropion. Four basic metabolites have been identified. They are the erythro- and threo-amino alcohols of bupropion, the erythro-amino diol of bupropion, and a morpholinol metabolite. These metabolites of bupropion are pharmacologically active, but their potency and toxicity relative to bupropion have not been fully characterized. Because the plasma concentrations of the metabolites are higher than those of bupropion, they may be of clinical importance.

The morpholinol metabolite (+/−)-(2R*,3R*)-2-(3-chlorophenyl)-3,5,5-trimethyl-2-morpholinol hydrochloride is believed to be formed from hydroxylation of the tert-butyl group of bupropion.

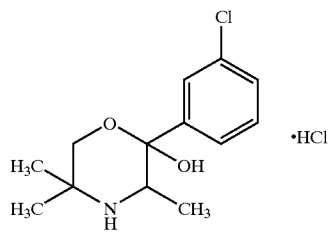

Morpholinol Metabolite of Bupropion HCl

SUMMARY OF THE INVENTION

It has now been discovered that despite the (−) form of the morpholinol metabolite predominating in human plasma samples, it is the (+) enantiomer, (+)-(2S, 3S)-2-(3-chlorophenyl)-3,5,5-trimethyl-2-morpholinol in which the activity resides.

Thus the present invention provides, in one aspect, a compound of formula (I), (+)-(2S, 3S)-2-(3-chlorophenyl)-3,5,5-trimethyl-2-morpholinol or pharmaceutically acceptable salts and solvates thereof.

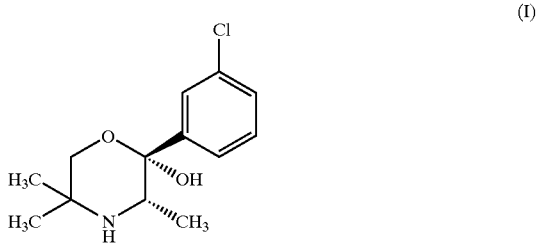

(I)

Another aspect of the invention is pharmaceutical compositions comprising a compound of formula (I) or pharmaceutically acceptable salts and solvates thereof together with one or more pharmaceutically acceptable carriers, diluents or excipients.

A further aspect of the present invention is the use of a compound of formula (I) or pharmaceutically acceptable salts and solvates thereof in therapy.

Yet another aspect of the invention provides methods of treating depression, attention deficit hyperactivity disorder (ADHD), obesity, migraine, pain, sexual dysfunction, Parkinson's disease, Alzheimer's disease, or addiction to cocaine or tobacco products in a human or animal subject comprising the administration to said subject of an effective amount of a compound of formula (I) or pharmaceutically acceptable salts and solvates thereof or pharmaceutical compositions thereof.

Yet another aspect of the present invention is the use of the compound of formula (I) or pharmaceutically acceptable salts and solvates thereof or pharmaceutical compositions thereof in the preparation of a medicament for the treatment of depression, attention deficit hyperactivity disorder (ADHD), obesity, migraine, pain, sexual dysfunction, Parkinson's disease, Alzheimer's disease, addiction to cocaine or tobacco products.

DETAILED DESCRIPTION OF THE INVENTION

Preparation

Figure 1:
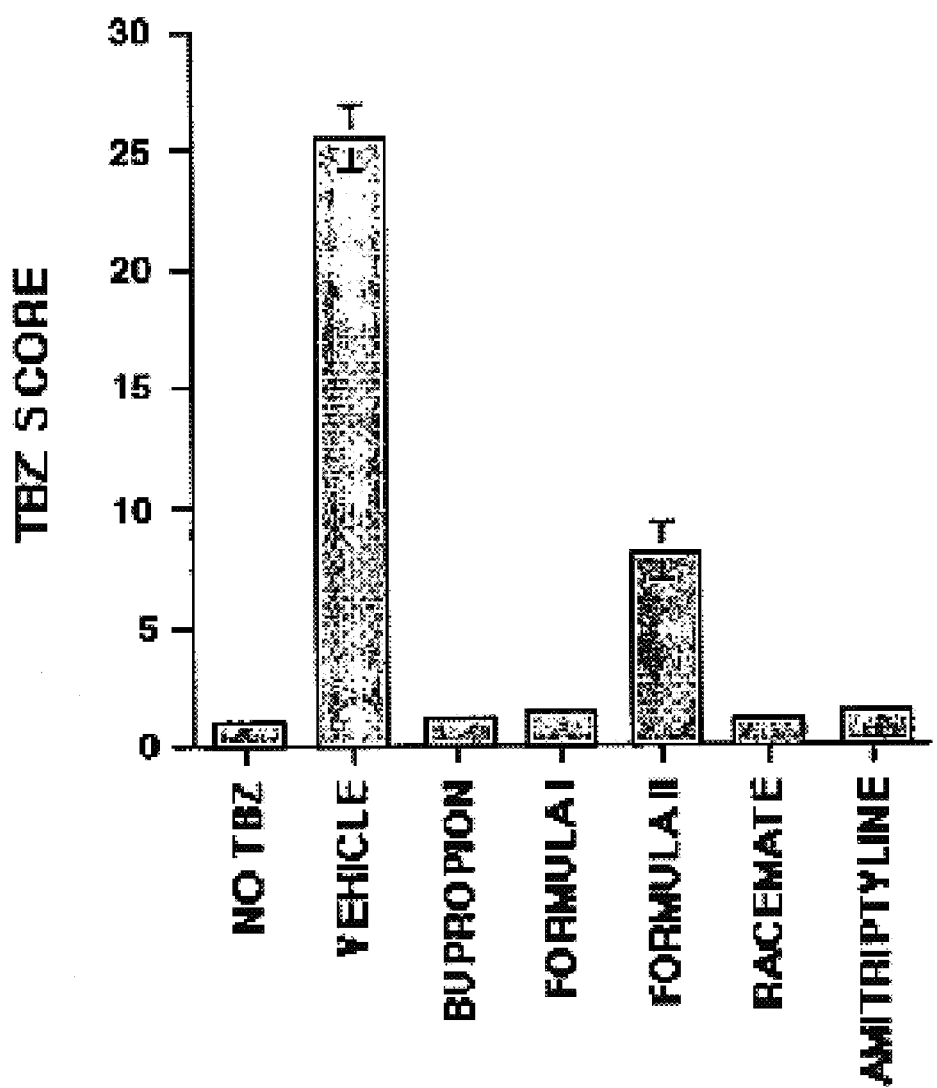
FIG. 1. Effect of Compounds at 25 mg/kg (ip) on TBZ-Induced Depression

The compound of formula (I) or pharmaceutically acceptable salts and solvates thereof may be prepared by first synthesizing the racemate of the morpholinol metabolite of bupropion and subsequently separating the (+) and (−) enantiomers of the racemate via HPLC.

The racemate of the morpholinol metabolite of bupropion hydrochloride ((+/−)-(2R*,3R*)-2-(3-chlorophenyl)-3,5,5- trimethyl-2-morpholinol hydrochloride) may be synthesized by the following process. To 3'-chloropropiophenone (10.0 g, 0.06 mol) in dioxane (50 mL) was added a solution of dioxane dibromide (14.9 g, 0.06 mol) in dioxane (50 mL). The reaction mixture was stirred for 2 h at ambient temperature and poured into a mixture of ice and water (500 mL). The mixture was extracted several times with methylene chloride. The combined extracts were dried ($Na_2SO_4$) and concentrated in vacuo to give 14.8 g (85%) of 2-bromo-3'-chloropropiophenone as a pale yellow oil. This was used without further purification. NMR (300 Mhz, $CDCl_3$); δ 7.99 (m, 1H), 7.90 (d, 1H), 7.57 (d, 1H), 7.44 (t, 1H), 5.22 (q, 1H), 1.91 (t, 3H).

To a solution of 2-bromo-3'-chloropropiophenone (19.3 g, 0.08 mol) in MeOH (100 mL) was added dropwise a solution of 2-amino-2-methyl-1-propanol (27.8 g, 0.31 mol) in methanol (200 mL) at ambient temperature. The mixture was stirred for 18 h and concentrated in vacuo. The residue was partitioned between water and diethyl ether. The combined organic phase was extracted with 10% aqueous hydrogen chloride. The combined aqueous acid extracts were chilled in an ice bath and made basic with 40% aqueous sodium hydroxide. The mixture was extracted with diethyl ether, the combined diethyl ether extracts were washed with water and saturated sodium chloride solution, dried ($K_2CO_3$) and concentrated in vacuo to give 15.0 g (75%) of (+/−)-(2R*,3R*)-2-(3-chlorophenyl)-3,5,5-trimethyl-2-morpholinol as an off-white solid.

(+/−)-(2R*,3R*)-2-(3-chlorophenyl)-3,5,5-trimethyl-2-morpholinol may be converted to (+/−)-(2R*,3R*)-2-(3-chlorophenyl)-3,5,5-trimethyl-2-morpholinol hydrochloride by the following process. A 6.0 g sample was dissolved in diethyl ether, chilled in an ice bath and ethereal hydrogen chloride added until the mixture was acidic. The resulting solid was filtered and recrystallized from ethanol/diethyl ether/ethereal hydrogen chloride mixtures to give 4.93 g of (+/−)-(2R*,3R*)-2-(3-chlorophenyl)-3,5,5-trimethyl-2-morpholinol hydrochloride as a white solid: m.p. 202–203° C. NMR (80 Mhz, DMSO-$d_6$); δ 10.9 (br, 1H), 8.85 (br, 1H), 7.60–7.4 (m, 5H), 4.04 (d, 1H), 3.50 (d, 1H), 3.37 (br s, 1H), 1.58 (s, 3H), 1.34 (s, 3H), 1.03 (d, 3H). Anal. Calcd for $C_{13}H_{19}Cl_2NO_2$: C, 53.43; H, 6.55; N, 4.79. Found: C, 53.54; H, 6.58; N, 4.75.

(+/−)-(2R*,3R*)-2-(3-chlorophenyl)-3,5,5-trimethyl-2-morpholinol hydrochloride may be converted back to its free base by the following process. A 3.0 g sample of (+/−)-(2R*,3R*)-2-(3-chlorophenyl)-3,5,5-trimethyl-2-morpholinol hydrochloride was dissolved in water (100 mL) and diethyl ether was added (200 mL). The mixture was chilled in an ice bath and the pH was adjusted to >10 with 1.0N aqueous sodium hydroxide. After stirring for 30 min., the phases were separated and the aqueous phase was extracted with diethyl ether. The combined diethyl ether extracts were dried ($Na_2SO_4$) and concentrated in vacuo to give 2.6 g of (+/−)-(2R*,3R*)-2-(3-chlophenyl)-3,5,5-trimethyl-2-morpholinol as a white solid. This was used without further purification for the chiral chromatography described below.

The (+) and (−) enantiomers of (+/−)-(2R*,3R*)-2-(3-chlorophenyl)-3,5,5-trimethyl-2-morpholinol may be separated by the following process. (+/−)-(2R*,3R*)-2-(3-chlorophenyl)-3,5,5-trimethyl-2-morpholinol (2.54 gms.) was dissolved in 250 ml of 2:8 Isopropyl alcohol:Hexane (both HPLC grade). A Daicel Chiralcel OD column (2×25 cm.) was equilibrated for one hour at 8 ml./min.in the elution solvent, 1:9:0.2 Isopropanol:Hexane:Diethylamine. The solution of the (+/−)-(2R*,3R*)-2-(3-chlorophenyl)-3,5,5-trimethyl-2-morpholinol was injected in 1 ml. aliquots by an automated Waters Prep LC 2000, using a Waters 510 EF pump for injections. Each run was 15 minutes in length, using the conditions listed before. The separated optical isomers were collected by fraction collector (Waters) at a 2% above baseline threshold, based on 2 absorbance units full scale at 240 nm (Waters 490E UV detector). Each optical isomer solution was evaporated on a rotary evaporator at 40 degrees Centigrade and aspirator vacuum. After drying for 6 hours under high vacuum at room temperature, optical isomer 1 weighed 1.25 gm. and optical isomer 2 weighed 1.26 gm.

The enantiomeric purity of each isomer was assayed by analytical chiral HPLC on a Waters 860 HPLC with 996 Photodiode Array detector, using a Daicel Chiralcel OD-H column (4.6×250 mm.) eluted with 1:9:0.2 Isopropyl alcohol:Hexane:Diethylamine at 1 m/min. Optical isomer 1 was 100% pure (R.T. 6.117 min.). Optical isomer 2 was 99.19% pure (R.T. 6.800 min.), containing 0.81% optical isomer 1 (R.T. 6.133 min.).

Hydrochloride salts of the separated enantiomers were obtained by the following processes. 1.25 g (0.005 mol) of optical isomer 1 (retention time 6.117 min) ((−)-(2R,3R)-2-(3-chlorophenyl)-3,5,5-trimethyl-2-morpholinol) was dissolved in diethyl ether. The solution was filtered and the filtrate was chilled in an ice-bath adding ethereal hydrogen chloride until the solution was acidic. After standing at ambient temperature for 24 h, the resulting solid was filtered, washed with diethyl ether and dried in a vacuum oven at 60° C. for 18 h to give 1.32 g (90%) of (−)-(2R,3R)-2-(3-chlorophenyl)-3,5,5-trimethyl-2-morpholinol hydrochloride as a white solid: mp 208–209° C. NMR (300 Mhz, DMSO-$d_6$); δ 9.72 (br, 1H), 8.76 (br, 1H), 7.54–7.41 (m, 5H), 3.98 (d, 1H), 3.52 (d, 1H), 3.37 (br s, 1H), 1.53 (s, 3H), 1.29 (s, 3H), 0.97 (d, 3H). Anal. Calcd for $C_{13}H_{19}Cl_2NO_2$: C, 53.43; H, 6.55; N, 4.79. Found: C, 53.35; H, 6.57; N, 4.71.

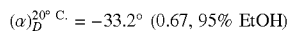

$(\alpha)_D^{20°\ C.} = -33.2°\ (0.67, 95\%\ EtOH)$ 1.26 g (0.005 mol) of optical isomer 2 (retention time 6.800 min) (+)-(2S,3S)-2-(3-chlorophenyl)-3,5,5-trimethyl-2-morpholinol) was dissolved in diethyl ether. The solution was filtered and the filtrate was chilled in an ice-bath adding ethereal hydrogen chloride until the solution was acidic. After standing at ambient temperature for 24 h, the resulting solid was filtered, washed with diethyl ether and dried in a vacuum oven at 60° C. for 18 h to give 1.36 g (93%) of (+)-(2S,3S)-2-(3-chlorophenyl)-3,5,5-trimethyl-2-morpholinol hydrochloride as a white solid: mp 208–209° C. NMR (300 Mhz, DMSO-$d_6$); δ 9.87 (br, 1H), 8.76 (br, 1H), 7.54–7.41 (m, 5H), 3.99 (d, 1H), 3.51 (d, 1H), 3.37 (br s, 1H), 1.54 (s, 3H), 1.30 (s, 3H), 0.98 (d, 3H). Anal. Calcd for $C_{13}H_{19}Cl_2NO_2$: C, 53.43; H, 6.55; N, 4.79. Found: C, 53.51; H, 6.58; N, 4.73.

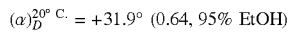

$(\alpha)_D^{20°\ C.} = +31.9°\ (0.64, 95\%\ EtOH)$

The absolute configuration of (+)-(2S,3S)-2-(3-chlorophenyl)-3,5,5-trimethyl-2-morpholinol was determined by the following x-ray crystallographic method. Crystal Data: $C_{13}H_{18}Cl_2NO_2$, M=291, Orthorhombic, space group $P2_12_12_1$, a=8.7348 (6), b=14.9824 (10), c=23.1605 (15) Å, V=3031 (4) Å$^3$, Z=8, Dc=1.267 Mgm$^{-3}$, F(000)= 1226.95. Of 12224 reflections measured. 3764 were unique and 2318 which had I>3.0σ(I) were used in subsequent calculations. Data was collected on a Siemens SMART diffractometer using omega scans and monochromated MoKα radiation (λ=0.71073 Å). The positions of all non-hydrogen atoms were determined by direct methods and refined anisotropically. The hydrogen positions were all located in difference syntheses and included in subsequent refinement cycles using a riding model and an idealized bond length of 0.96 Å. The absolute configuration was determined by refinement of the Rogers' parameter and confirmed by an analysis of the 185 best Bijvoet intensity differences which indicated a probability of 0.006 that the model was in error. Least squares refinement minimized $\Sigma w(\Delta F)^2$ with weights based on counter statistics. The final agreement factors were $R_f$=0.064 (0.108 for all data), $R_w$=0.068 (0.081 for all data), and GoF=1.93. References included E. J. Gabe, Y. Le Page, J.-P. Charland, F. L. Lee and P. S. White, Journal of Applied Crystallography, 22, 384–387 (1989) and D. Rogers, Acta Crystallographica, A37, 734–741, 1981.

According to a modified preparation process, as set out in Scheme 1 below, a solution of 3'-chloropropiophenone in dichloromethane as solvent may be treated with bromine to afford the bromoketone. After a wash with a suitable base, for example aqueous sodium hydrogencarbonate solution, to remove dissolved hydrogen bromide, the dichloromethane solvent is preferably replaced by acetonitrile. 2-Amino-2-methylpropan-1-ol is added to the bromoketone solution and the resulting mixture stirred at 40° C. for ~18 hours. This effects displacement of the bromine with concomitant cyclisation to give a racemic mixture of the enantiomeric diastereoisomers of hydroxybupropion.

Scheme 1

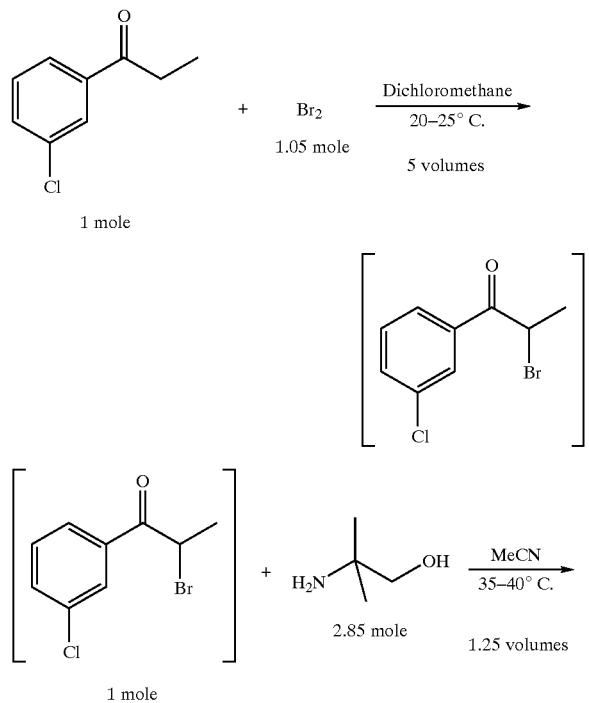

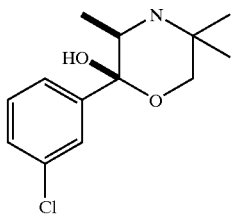

When a mixture of enantiomeric bases interacts with an optically active acid, diastereomeric salts are formed. These diastereomeric salts have different physical properties and can advantageously be separated by methods based on these differences, which methods include, but are not limited to, distillation, chromatographic separation, and fractional crystallisation.

Accordingly, an aspect of the present invention is a process for preparing optically pure (+)-(2S, 3S)-2-(3-chlorophenyl)-3,5,5-trimethyl-2-morpholinol or a pharmaceutically acceptable salt or solvate thereof which comprises treating the racemic 2-(3-chlorophenyl)-3,5,5-trimethyl-2-morpholinol with a chiral acid under suitable reaction conditions to form a mixture of diastereomeric salts; isolating from the mixture of the diastereomeric salts a chiral salt of (+)-(2S, 3S)-2-(3-chlorophenyl)-3,5,5-trimethyl-2-morpholinol; and contacting the chiral salt of (+)-(2S, 3S)-2-(3-chlorophenyl)-3,5,5-trimethyl-2-morpholinol with a base.

Thus, resolution of racemic hydroxybupropion may be achieved by using a chiral acid resolving agent according to Scheme 2 below. Following screening studies of a range of chiral acids it has been found that particularly efficacious resolution (resulting in the preparation of the compound of formula (I) with an enantiomeric excess—95%) can be achieved using chiral di-p-toluyltartaric acid (particularly di-p-toluyl-L-tartaric acid (L-DTTA)) in an appropriate solvent. Preferred solvents include ethanol, IMS and acetonitrile. A more detailed process is set out in Example A below.

Scheme 2

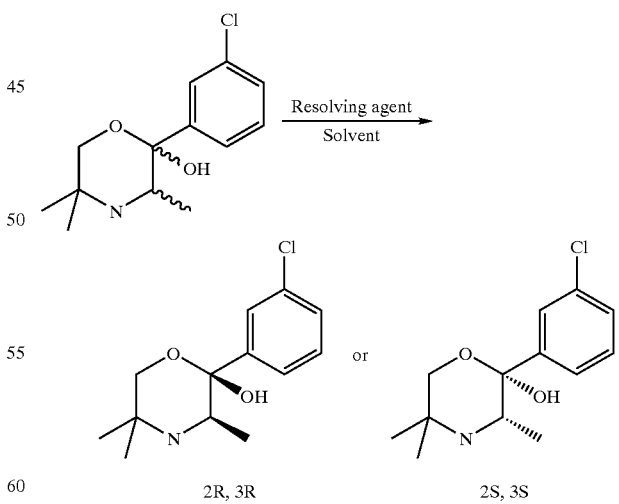

Compared to using ethanol alone as the solvent, a modification involving addition of water gave an improved yield, as demonstrated in Example B below.

Reaction between the racemic hydroxybupropion and the chiral acid preferably involves using about 1.4 to about 2.0 molar equivalents of chiral acid, more preferably about 1.5 to about 2.0 equivalents, to give efficient and reproducable resolution. The Table below shows the impact of chiral acid stoichiometry on enantiomeric excess, as determined by chiral HPLC.

TABLE effect of stochiometry of chiral acid on enantiomeric excess

| Conditions | % ee |
|---|---|
| 1 eq, (−) DTTA, EtOH | 10.9 S |
| 1.25 eq, (−) DTTA, EtOH | 26.4 S |
| 1.5 eq, (−) DTTA, EtOH | 93.5 S |
| 2.0 eq, (−) DTTA, EtOH | 90.5 S |

A further preferred modification to achieve particularly reproducible resolution is to add the racemic hydroxybupropion as a solution to the DTTA as a solution.

The purity of the DTTA salt can be improved by methods well known to the person skilled in the art, if appropriate, for example by further crystallisation. For example, the DTTA salt may be dissolved in methanol and the solution treated with water to enable crystallisation.

Preparation of the compound of formula (I) involves reaction of the appropriate crystallised DTTA salt with a suitable base. Suitable bases include sodium hydrogencarbonate, potassium carbonate and aqueous ammonia (including ammonium hydroxide). Other suitable bases include potassium hydroxide and sodium hydroxide.

Subsequent treatment of the chiral free base compound of formula (I), for example with hydrogen chloride in a suitable solvent (such as isopropanol, and isopropanol/ethylacetate) yields the desired chiral hydrochloride salt. Recrystallisation of this salt may be carried out by methods well known to the person skilled in the art, for example using methanol/ethyl acetate.

3-chloropropiophenone may suitably be converted to the relevant DTTA salt without isolation of the racemic hydroxybupropion, as illustrated in Example C below.

As set out in Example D below, advantageously a single solvent, ethyl acetate, can predominantly be used both in the preparation of the DTTA salt and in subsequent steps to prepare both the compound of formula (I) and its hydrochloride salt. This has positive benefits on cost and throughput, as well as environmental benefits, for example easier recovery of solvent for reuse.

Dosage and Formulation

The amount of compound of formula (I) required to achieve the desired therapeutic effect will, of course depend on a number of factors, for example, the mode of administration, the recipient and the condition being treated. In general, the daily dose will be in the range of 0.02 to 5.0 mg/kg. More particular ranges include 0.02 to 2.5 mg/kg, 0.02 to 1.0 mg/kg, 0.02 to 0.25 mg/kg, 0.02 to 0.15 mg/kg and 0.02 to 0.07 mg/kg.

The compound of formula (I) may be employed in the treatment of depression, attention deficit hyperactivity disorder (ADHD), obesity, migraine, pain, sexual dysfunction, Parkinson's disease, Alzheimer's disease, addiction to cocaine or tobacco products as the compound per se, but is preferably presented with one or more pharmaceutically acceptable carriers, diluents or excipients in the form of a pharmaceutical formulation. The carriers, diluents and exipients must, of course, be acceptable in the sense of being compatible with the other ingredients of the formulation and must not be deleterious to the recipient. The carrier may be a solid or a liquid, or both, and is preferably formulated with the agent as a unit-dose formulation, for example, a tablet.

The formulations include those suitable for oral, rectal, topical, buccal (e.g. sub-lingual) and parenteral (e.g. subcutaneous, intramuscular, intradermal or intravenous) administration.

Formulations suitable for buccal (sub-lingual) administration include lozenges comprising a compound of formula (I) in a flavoured base, usually sucrose and acacia or tragacanth, and pastilles comprising the agent in an inert base such as gelatin and glycerin or sucrose and acacia.

Formulations of the present invention suitable for parenteral administration conveniently comprise sterile aqueous preparations of a compound of formula (I), preferably isotonic with the blood of the intended recipient. These preparations are preferably administered intravenously, although administration may also be effected by means of subcutaneous, intramuscular, or intradermal injection. Such preparations may conveniently be prepared by admixing the agent with water and rendering the resulting solution sterile and isotonic with the blood.

Formulations suitable for rectal administration are preferably presented as unit-dose suppositories. These may be prepared by admixing a compound of formula (I) with one or more conventional solid carriers, for example, cocoa butter, and then shaping the resulting mixture.

Formulations suitable for topical application to the skin preferably take the form of an ointment, cream, lotion, paste, gel, spray, transdermal patch, aerosol, or oil. Carriers which may be used include vaseline, lanolin, polyethylene glycols, alcohols, and combinations of two or more thereof.

It should be understood that in addition to the ingredients particularly mentioned above, the formulations may include other agents conventional in the art having regard to the type of formulation in question.

Biological Activity

Biological activity of the compound of formula (I) was demonstrated by in vitro uptake models and the tetrabenazine-induced behavioural depression model. The racemic morpholinol metabolite, (+/−)-(2R*,3R*)-2-(3-chlorophenyl)-3,5,5-trimethyl-2-morpholinol, is referred to herein as "Racemate". The (−) form of the morpholinol metabolite is (−)-(2R, 3R)-2-(3-chlorophenyl)-3,5,5-trimethyl-2-morpholinol or pharmaceutically acceptable salts and solvates thereof and is referred to herein as a compound of formula (II):

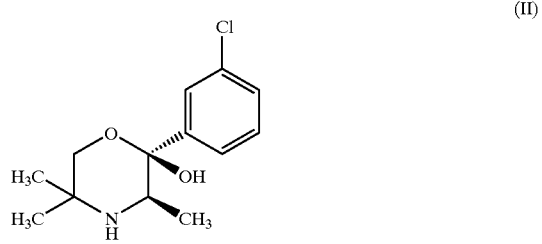

(II)

In vitro Synaptosomal Uptake Experiments

In vitro uptake was determined, as reported previously, using synaptosomes prepared from rat caudoputamen (for dopamine uptake) and hypothalamus (for NA and serotonin uptake) using [$^3$H]-dopamine, [$^3$H]-NA and [$^3$H]-serotonin as transport substrates, respectively. See Eckhardt, S. B., R. A. Maxwell, and R. M. Ferris, A Structure-Activity Study of the Transport Sites for the Hypothalamic and Striatal Catecholamine Uptake Systems. Similarities and differences. *Molecular Pharmacology*, 21: p. 374–9,1982.

Synaptosomes for use in obtaining in vitro uptake data were prepared from hypothalamus or striatum by gently homogenizing the tissue in a 0.3 M sucrose/25 mM Tris pH 7.4 buffer containing iproniazid phosphate to inhibit monoamine oxidase. The homogenate was centrifuged at 1100×g at 4° C. for 10 min and the supernatant was used for uptake studies. The supernatant (~1 mg tissue protein) was incubated with Km concentrations of [$^3$H]-noradrenaline, [$^3$H]-dopamine or [$^3$H]-serotonin at 37° C. for 5 minutes in Modified Krebs-Henseleit buffer (118 mM NaCl, 5 mM KCl, 25 mM NaHCO$_3$, 1.2 mM NaH$_2$PO$_4$, 1.2 mM MgSO$_4$, 11 mM Dextrose, 2.5 mM CaCl$_2$) in the absence and presence of drug. Under these conditions uptake was linear with respect to both for substrate and tissue (with <5% total substrate transported). Non-specific uptake was defined as uptake at 0° C. [$^3$H]-substrate, which had been transported into synaptosomes, was separated from free [$^3$H]-substrate by filtration over GF/B filters and washing with cold Krebs-Henseleit buffer. The filters were counted for tritum in a liquid scintillation spectrometer.

The data for in vitro synaptosomal uptake are presented as Table 1. Among the 2 enantiomers of the morpholinol metabolite of bupropion, the (+) enantiomer, the compound of formula (I), inhibited noradrenaline (NA) uptake with an IC$_{50}$ of 1.1 µM. In contrast, the (−) enantiomer was ineffective at a concentration of 30 µM. On dopamine (DA) uptake, the compound of formula (I) had an IC$_{50}$ of ~10 µM while the (−) enantiomer was inactive at 30 µM. Neither compound inhibited serotonin uptake at 30 µM.

For comparison, Wellbutrin® was equipotent for inhibiting DA and noradrenaline uptake with IC$_{50}$ values of 1.9 and 2.2 µM, and did not inhibit serotonin uptake at 30 µM. Imipramine (a non-specific tricyclic antidepressant) inhibited NA uptake and serotonin uptake with IC$_{50}$ values of 0.072 and 0.24 µM, respectively.

The compound of formula (I) was approximately twice as potent as Wellbutrin® as an NA inhibitor but, unlike the latter, was approximately 10-fold less potent as an inhibitor of dopamine uptake. These data are consistent with the observed noradrenergic actions of Wellbutrin® and the racemic morpholinol metabolite of bupropion, (+/−)-(2R*, 3R*)-2-(3-chlorophenyl)-3,5,5-trimethyl-2-morpholinol hydrochloride, (306U73) in vivo, at their respective anti-TBZ doses (Cooper, B. R., et al, *Neuropsychopharmacology*, 11: p. 133–41,1994). Behavioral and electrophysiological data suggest that the effects of Wellbutrin® are mediated by a noradrenergic mechanism (ibid).

Tetrabenazine-Induced Behavioural Depression Experiments

Tetrabenazine (TBZ)-induced behavioural depression was used as an in vivo measure of antidepressant activity. The test has been validated with a wide range of antidepressants, known to act through noradrenergic mechanisms (Cooper B. R. et al, "Animal models used in the prediction of antidepressant effects in man", J. Clin. Psychiatry 44: 63–66, 1983). Moreover, the test was also used to identify Wellbutrin® as an anti-depressant. Briefly, animals were injected with the candidate agent (p.o. or i.p.) 30 minutes before receiving an i.p. injection of tetrabenazine (35 mg/kg, as the HCl salt—prepared fresh for each use). Assessments were performed 30 minutes thereafter and included: locomotor activity (1–4 scale); ptosis (1–4 scale) and body temperature as described previously (Cooper, B. R., J. L. Howard, and F. E. Soroko, Animal models used in prediction of antidepressant effects in man (*Journal of Clinical Psychiatry*, 44: p. 63–6,1983). In all studies, the scientist performing the assessments was blind to the treatments. All parameters were weighted equally to give a "lumped" score (X) through the following algorithm:

$$X=(1+\text{Ptosis score})/(\text{Activity score}*[\text{Temp,treated}/\text{Temp,control}])$$

Results from the tetrabenazine-induced behavioural depression model are as follows. Assessed in vivo at 25 mg/kg (ip) the compound of formula (I), the racemate, Wellbutrin® and, for comparison, amitryptyline all abolished the tetrabenazine-induced behavioural depression. In contrast, the (−) enantiomer showed only modest activity (FIG. 1).

Figure 2:
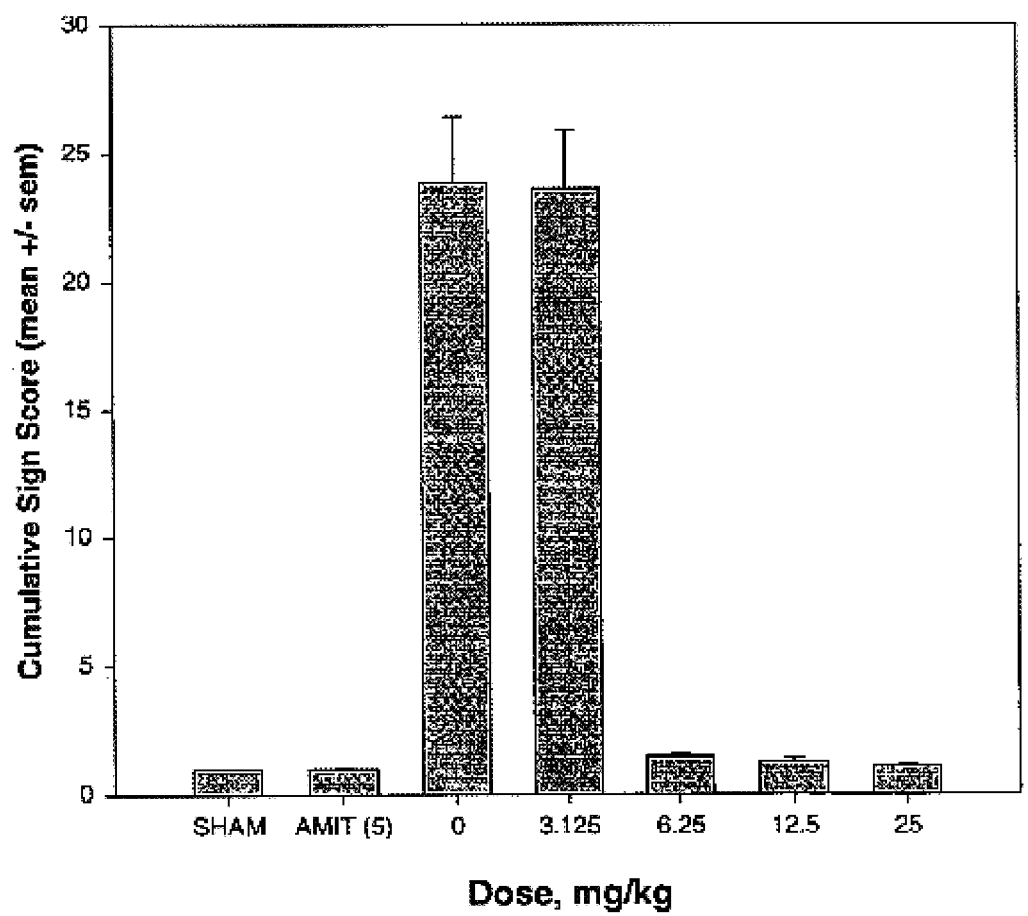
FIG. 2. Dose Response of Compound of Formula I Against TBZ-Induced Depression (Compounds administered 30 minutes prior to TBZ, Male, CD-1 Mice, i.p., n=6)
Figure 3:
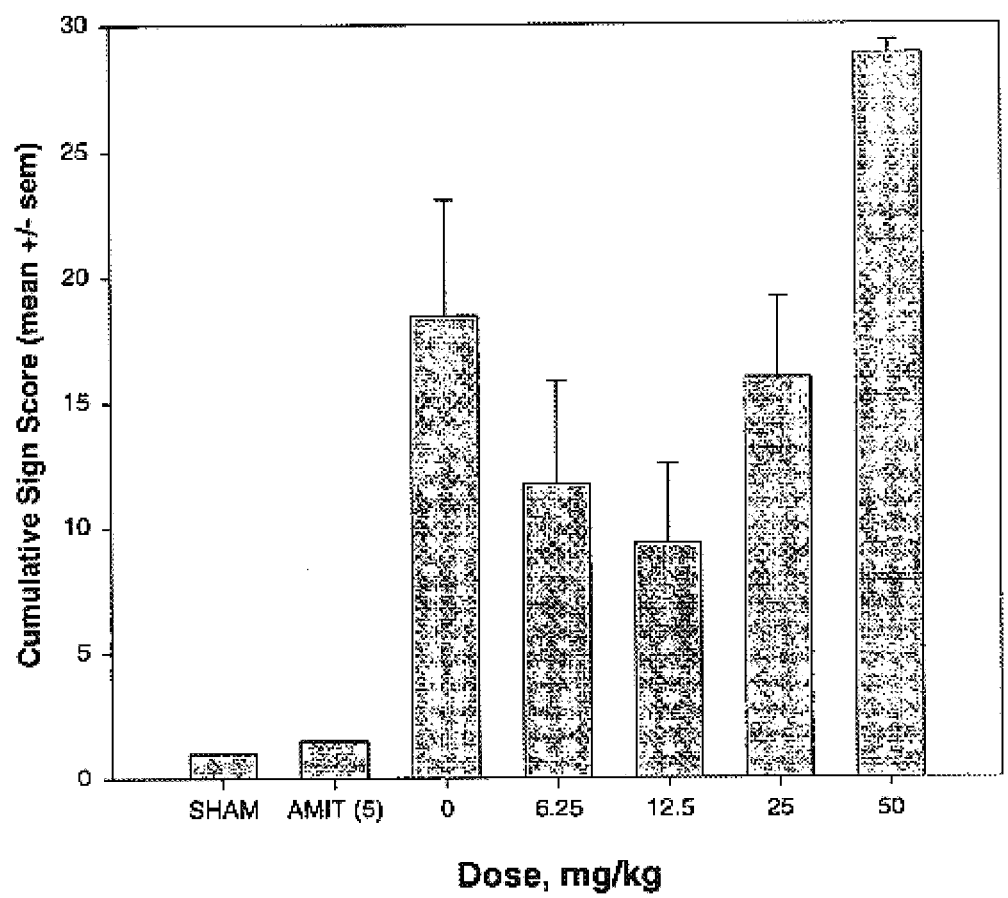
FIG. 3. Dose Response of Compound of Formula II Against TBZ-Induced Depression (Compounds administered 30 minutes prior to TBZ, Male, CD-1 Mice, i.p., n=6)

In the TBZ model of behavioural depression, activity resided in the compound of formula (I). When analysed in a dose-effect study with TBZ, the activity showed a sharp increase in activity between 3 mg/kg and 6 mg/kg (ip) (FIG. 2). The compound of formula II, in comparison, did not possess dose-related activity and, at 50 mg/kg, appeared to worsen the animal's condition (FIG. 3). In FIGS. 2 and 3, AMIT (5) refers to amitryptiline dosed at 5 mg/kg and SHAM refers to a control group of animals that have received no medication at all.

Since the TBZ test has been predictive of anti-depressants acting through noradrenergic mechanisms and the compound of formula (I) is an inhibitor of noradrenaline uptake and Wellbutrin® is metabolised to this morpholinol in vivo, the data suggest that the anti-depressant activity of Wellbutrin® is likely to result from the effects of the compound of formula (I). (Welch, R. M., A. A. Lai, and D. H. Schroeder, Pharmacological significance of the species differences in bupropion metabolism. *Xenobiotica*, 17: p. 287–98,1987).

By extension, other activities of Wellbutrin® could be attributed to the compound of formula (I). In particular, a noradrenergic mechanism is common to agents used to treat ADHD (e.g. methylphenidate and amphetamine). While the molecular mechanism for Wellbutrin's effects on smoking cessation is less well understood, a catecholaminergic pathway is thought to participate in the behavioural reinforcing properties of nicotine. Wellbutrin® (and, by extension, the compound of formula (I)), by augmenting NA release into brain synapses, could mimic some of the actions of nicotine and, thus, decrease the signs associated with nicotine withdrawal. Additionally, amphetamines have been used to treat obesity. The addictive properties of amphetamine, however, preclude its use for most obese patients. Wellbutrin® causes weight loss and, like amphetamine, acts through a noradrenergic mechanism. (Zarrindast, M. R. and T. Hosseini-Nia, Anorectic and behavioural effects of bupropion. *General Pharmacology*, 19: p. 201–4,1988 and Harto-Truax, N., et al., Effects of Bupropion on Body Weight. *Journal of Clinical Psychiatry*, 44: p. 183–6,1983). However, unlike amphetamine, Wellbutrin® is not addictive. (Lamb, R. J. and R. R. Griffiths, Self-administration in Baboons and the Discriminative Stimulus Effects in Rats of Bupropion, Nomifensine, Diclofensine and Imipramine. *Psychopharmacology*, 102: p. 183–90,1990; Bergman, J., et al., Effects of Cocaine and Related Drugs in Nonhuman Primates. III. Self-administration by Squirrel Monkeys. *Journal of Pharmacology & Experimental Therapeutics*, 251: p. 150–5,1989 and Johanson, C. E.; and J. E. Barrett, The Discriminative Stimulus Effects of Cocaine in Pigeons. *Journal of Pharmacology & Experimental Therapeutics*, 267: p. 1–8,1993). By extension, the compound of formula (I) would also be expected to have efficacy in obesity and cocaine addiction.

Safety and Toxicity

Additional dose-ranging studies were performed to determine the range of safe does for the isomers and the racemate. Animals were observed for the presence of serious adverse events (e.g. seizures and deaths) following administration of the compounds of formula I, formula II or the racemate by the oral and intraperitoneal (i.p.) routes. The data are presented as Table II.

Administered orally, at 100 mg/kg p.o., seizures were observed with the compound of formula II and the racemate but not with the compound of formula I. Seizures were observed in all of the animals with all 3 compounds when dosed at 300 mg/kg. Additionally, at the 300 mg/kg oral dose resulted in 100 and 80% lethality for the compound of formula II and the racemate while no deaths were observed with the compound of formula I.

Administered i.p., all of the compounds produced seizures at 100 mg/kg. No deaths were observed with the compound of formula I whereas the compound of formula II and the racemate resulted in lethality of 100% and 20%, respectively. At the 300 mg/kg i.p. dose all of the lethality was observed for all of the compounds.

TABLE I

Effects on Uptake In Vitro

| Compound | IC50 ($\mu$M) | SEM |
|---|---|---|
| [$^3$H]-Dopamine Uptake | | |
| Bupropion | 1.9 | 0.15 |
| Formula (I) | 9.3 | 0.41 |
| Formula (II) | >100 | |
| [$^3$H]-Noradrenaline Uptake | | |
| Bupropion | 2.2 | 0.7 |
| Formula (I) | 1.1 | 0.07 |
| Formula (II) | >30 | |
| Imipramine | 0.072 | 0.020 |
| [$^3$H]-Serotonin Uptake | | |
| Bupropion | >30 | |
| Formula (I) | >30 | |
| Formula (II) | >100 | |
| Imipramine | 0.24 | 0.03 |

TABLE 2

Adverse Events Associated with Compounds of Formula I, II and Racemate

| Compound | Route | Dose (mg/kg) | Seizures (%) | Time to Seizures (min) | % Died | Time to Death (min) |
|---|---|---|---|---|---|---|
| Formula I | i.p. | 100 | 100 | 3.93 | 0 | n/a |
| Formula I | p.o. | 100 | 0 | n/a | 0 | n/a |
| Formula I | i.p. | 300 | 100 | 3.95 | 100 | 6 |
| Formula I | p.o. | 300 | 100 | 11.23 | 0 | n/a |
| Formula II | i.p. | 100 | 20 | 5 | 100 | 7 |
| Formula II | p.o. | 100 | 100 | 7.2 | 0 | n/a |
| Formula II | i.p. | 300 | 100 | 1.1 | 100 | 6 |
| Formula II | p.o. | 300 | 100 | 6.8 | 100 | 7 |
| Racemate | i.p. | 100 | 100 | 3 | 20 | 14 |
| Racemate | p.o | 100 | 100 | 9.2 | 0 | n/a |
| Racemate | i.p | 300 | 100 | 3 | 100 | 3 |
| Racemate | p.o | 300 | 100 | 6.8 | 80 | 7 |

N/a denotes that the effect was not observed and, therefore, no percentage was given.

Further Synthetic Examples

The products and intermediates of Examples A to D were confirmed as having the indicated structures by MS and/or NMR analysis.

EXAMPLE A

A flask was charged with racemic hydroxybupropion (1 wt) and (–)-di-toluyl-L-tartaric acid (2.26 wt) and to this was added ethanol (10 vol). The resulting mixture was then heated to 50° C. As the mixture is warmed almost all the solid dissolves. On reaching 31° C., a fine precipitate is observed and a seed of the desired salt was added. As the mixture approaches 50° C. further precipitation is observed and the temperature maintained at 50° C. for 1 hr. The reaction was then allowed to cool slowly to room temperature and left to stir overnight. The mixture was then cooled to ca 5° C. for 1 hr and the solid filtered. A slow filtration (ca 1 h) was observed due to a thick bed of solid. The contents of the flask were washed out with ethanol (1 vol) and the filter cake washed with ethanol (4 vol). The resulting white solid was dried under vacuum at 45° C. for 5 hrs affording 23.03 g, 36.7%th of the desired salt (95%ee by chiral HPLC analysis).

The salt was then slurried in saturated sodium hydrogencarbonate (40 vol) and this was extracted with ethyl acetate (40 vol). HPLC analysis of the two layers showed the absence of free amine in the aqueous layer and this was discarded, however the organic fraction still contained acid. Further ethyl acetate (160 vol) was added in an attempt to dissolve the remaining solid in the organic layer. Two further extractions with aqueous sodium hydrogencarbonate proved unfruitful in removing the acid. The organic layer was then washed with aqueous potassium carbonate (2×100 vol) which effected an improved removal of acid. The organic layer now contained no acid (by HPLC) and the combined fractions were evaporated to dryness to afford a white solid, 9.4 g, 102.4%th (37.6%th wrt racemic amine) (95%ee by chiral HPLC analysis) which was confirmed by MS and NMR analysis to be the compound of formula (I).

The reactions were analysed on Chiralcel OD-H (25 cm, 2:98 EtOH:C7, 1 ml/min, 215 nm). For the final product, the analysis showed a retention time of 7.6 min for the compound of formula (I).

EXAMPLE B

The hydrochloride salt of racemic hydroxybupropion (1 wt) was dissolved in water (10 vols) and ethyl acetate was added (20 vol). The mixture was chilled in an ice bath and the pH was adjusted to 9 with 1N aqueous sodium hydroxide (3 vol). After stirring for 30 min., the organic phase was separated and ethyl acetate was partially evaporated to 3 vol, then EtOH (10 vol) was added and the obtained mixture evaporated again to 3 vol. The operation was repeated and at the end the total volume was adjusted to 4.2 vol with EtOH. (–)-Di-toluyl-L-tartaric acid (1.89 wt, 1.4 eq) was added and the mixture was stirred at room temperature for 5 h. Water was added (1.7 vol) and the suspension was stirred at room temperature overnight. After cooling at ca 5° C. and stirring for 2 h the solid was filtered, washed with ethanol and dried under vacuum at 40° C. for 5 hrs to give the desired DTTA salt of the compound of formula (I) (yield=41%, e/e=96.6).

EXAMPLE C

The crude 2-bromo-3'-chloropropiophenone is diluted with acetonitrile (3.6 vol) at room temperature. To this mixture, 2-amino-2-methyl-propanol (1.1 vol) in acetonitrile (3.6 vol) is added over 20 min and the mixture is stirred at room temperature for 22 hr. EtOAc (15 vol) and water (15 vol) are added and the resulting mixture was stirred at room temperature until a complete solubilization is obtained. The organic layer is separated and washed with water (2×7.5 vol) and finally it is concentrated to 4 vol. EtOH 95% (15 vol) is added and the obtained solution is re-evaporated to 4 vol. The operation is repeated and at the end the volume is adjusted to reach the final 5.4 vols with EtOH 95%. Di-p-toluoyl-L-tartaric acid (2.4 wt) is added and the obtained mixture is stirred at room temperature for 20 hrs (a white precipitate is obtained) then cooled to 0 to 5° C. and stirred for 2 hrs. The solid is filtered, washed with cold EtOH 95% (1 vol) and dried under vacuum at 40° C. for 20 hrs to give the desired DTTA salt of the compound of formula (I).

EXAMPLE D

3'-chloropropiophenone in dichloromethane (5 volumes) is treated with bromine at 20–25° C. at a rate determined by the reaction rate of the bromine. On completion of the addition the mixture is stirred for one hour and then the reaction mixture is quenched into aqueous sodium bicarbonate solution (3 volumes) and the organic phase washed with water (1 volume) to remove the hydrogen bromide by-product before being concentrated to dryness resulting in a mobile oil.

The residual oil is diluted with acetonitrile and treated with a solution of 2-amino-2-methyl-1-propanol (2.85 eq.) in acetonitrile (1.25 volumes in total) over half an hour at 30–35° C. The reaction mixture is diluted with ethyl acetate and demineralised water and the two phases are separated. The organic phase is washed with demineralised water. The two aqueous layers are combined and washed with ethyl acetate. The two organic phases are combined and washed twice with aqueous sodium chloride. The resulting organic phase is then concentrated and the solvent changed to industrial methylated spirit (IMS) by 'put and take' distillation.

The IMS solution is added to a solution of di-p-toluoyl-L-tartaric acid (1.75 eq.) in IMS at 45–50° C. The mixture is stirred at reflux for 30 minutes to 1 hour, cooled to 20–25° C. over 2 hours and stirred at 20–25° C. for 16–20 hours to allow the product to crystallise. The product is filtered, washed three times with IMS and dried at 50–55° C. under vacuum to give the chiral DTTA salt of the compound of formula (I).

The DTTA salt is suspended in 1:1 ethyl acetate/demineralised water and treated with aqueous ammonium hydroxide (3.55 eq.). The aqueous phase is separated and the organic phase washed with demineralised water before being concentrated to low volume. Ethyl acetate and methanol are added and the solution treated with a solution of hydrochloric acid (5-6M) in 2-propanol/ethyl acetate at 40–45° C.

The mixture is cooled to 10–15° C. and stirred at that temperature for 2–4 hours. The product is isolated in a centrifuge, washed twice with 49:1 ethyl acetate:methanol and dried at 75–80° C. under vacuum.

The hydrochloride salt of the compound of formula (I) thus prepared is dissolved in methanol and the solution filtered. Ethyl acetate is added over approximately 1 hour to crystallise the product. The slurry is then stirred for 3 hours at 20–25° C. before being isolated and washed twice with ethyl acetate. The product is then dried under vacuum at 50–55° C. The dry product is then sieved to ensure homogeneity. The enantiomeric purity of the product (the hydrochloride salt of the compound of formula (I)) was determined to be 100% ee.

What is claimed is:

1. A process for preparing optically pure (+)-(2S, 3S)-2-(3-chlorophenyl)-3,5,5-trimethyl-2-morpholinol or a pharmaceutically acceptable salt or solvate thereof which comprises
    treating racemic 2-(3-chlorophenyl)-3,5,5-trimethyl-2-morpholinol with di-p-toluyl-L-tartaric acid under suitable reaction conditions and in a solvent to form a mixture of diastereomeric salts, wherein the solvent comprises at least one solvent selected from the group consisting of ethanol, ethanol and water, industrial methylated spirit (IMS), and acetonitrile;
    isolating from the mixture of the diastereomeric salts a chiral salt of (+)-(2S, 3S)-2-(3-chlorophenyl)-3,5,5-trimethyl-2 -morpholinol; and
    contacting the chiral salt of (+)-(2S, 3S)-2-(3-chlorophenyl)-3,5,5-trimethyl-2-morpholinol with a base.

2. The process as claimed in claim 1, wherein the solvent is selected from ethanol, industrial methylated spirit (IMS) and acetonitrile.

3. The process as claimed in claim 1, wherein the solvent is a mixture of ethanol and water.

4. The process as claimed in claim 1, wherein the base is selected from sodium hydrogencarbonate, potassium carbonate, aqueous ammonia, and ammonium hydroxide.

5. The process as claimed in claim 1, wherein the di-p-toluyl-L-tartaric acid is used in about 1.4 to about 2.0 equivalents relative to the racemic 2-(3-chlorophenyl)-3,5,5-trimethyl-2-morpholinol.

6. The process as claimed in claim 5, wherein about 1.5 to about 2.0 equivalents of di-p-toluyl-L-tartaric acid are used.

7. The process as claimed in claim 1, wherein the racemic 2-(3-chlorophenyl)-3,5,5-trimethyl-2-morpholinol solution is added as a solution to the di-p-toluyl-L-tartaric acid as a solution.

8. The process as claimed in claim 1, wherein said solvent comprises ethanol.

9. The process as claimed in claim 1, wherein said solvent comprises industrial methylated spirit (IMS).

10. The process as claimed in claim 1, wherein said solvent comprises acetonitrile.

11. A process for preparing optically pure (S,S)-2-(3-chlorophenyl)-2-hydroxy-3,5,5-trimethyl-morpholinol or a pharmaceutically acceptable salt or solvate thereof which comprises:
    brominating 3-chloropropiophenone to form an intermediate;
    contacting the intermediate with 2-amino-2-methyl-1-propanol under suitable reaction conditions and in a suitable solvent for the formation of racemic 2-(3-chlorophenyl)-2-hydroxy-3,5,5-trimethyl-morpholinol, wherein said solvent comprises at least one solvent selected from the group consisting of ethanol, ethanol and water, industrial methylated spirit (IMS), and acetonitrile;
    contacting the racemic 2-(3-chlorophenyl)-2-hydroxy-3,5,5-trimethyl-morpholinol with di-p-toluyl-L-tartaric acid under suitable reaction conditions to form a mixture of diastereomeric salts;
    isolating from the mixture of the diastereomeric salts a chiral salt of (S,S)-2-(3-chlorophenyl)-2-hydroxy-3,5,5-trimethyl -morpholinol; and
    contacting the chiral salt of (S,S)-2-(3-chlorophenyl)-2-hydroxy-3,5,5-trimethyl-morpholinol with a base.

12. The process of claim 11, wherein the formation of diastereomeric salts and/or isolation of the chiral salt of (S,S)-2-(3-chlorophenyl)-2-hydroxy-3,5,5-trimethyl-morpholinol gives a mother liquor.

13. The process of claim 11, wherein the base is selected from the group consisting of potassium carbonate, potassium hydroxide, sodium hydroxide, and ammonium hydroxide.

14. The process of claim 11, wherein the solvent is selected from ethanol, industrial methylated spirit (IMS) and acetonitrile.

15. The process of claims 11, wherein the solvent is a mixture of ethanol and water.

16. The process of claim 11, wherein said solvent comprises ethanol.

17. The process of claim 11, wherein said solvent comprises industrial methylated spirit (IMS).

18. The process of claim 11, wherein said solvent comprises acetonitrile.

* * * * *